US006871794B2

(12) United States Patent
McEwen

(10) Patent No.: US 6,871,794 B2
(45) Date of Patent: Mar. 29, 2005

(54) LIQUID DISPERSION DEVICE

(75) Inventor: Charles Nehemiah McEwen, Newark, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 229 days.

(21) Appl. No.: 10/427,785

(22) Filed: May 1, 2003

(65) Prior Publication Data

US 2004/0217188 A1 Nov. 4, 2004

(51) Int. Cl.[7] .................... A24F 25/00; A61L 9/04
(52) U.S. Cl. .................. 239/44; 239/45; 239/50
(58) Field of Search .................... 239/43, 44, 45, 239/49, 50, 34, 86, 145, 583

(56) References Cited

U.S. PATENT DOCUMENTS

| | | |
|---|---|---|
| 1,994,932 A | 3/1935 | Vidal |
| 2,597,195 A | 5/1952 | Smith et al. |
| 2,802,695 A | 8/1957 | Johnson |
| 2,804,291 A | 8/1957 | Segerstad |
| 2,942,090 A | 6/1960 | Diehl |
| 3,288,556 A | 11/1966 | Weber, III |
| 3,431,393 A | 3/1969 | Katsuda |
| 3,482,929 A | 12/1969 | Gentil |
| 3,550,853 A | 12/1970 | Gray |
| 3,633,881 A | 1/1972 | Yurdin |
| 3,780,260 A | 12/1973 | Elsner |
| 4,020,321 A | 4/1977 | Oswald |
| 4,084,079 A | 4/1978 | Costello |
| 4,286,754 A | 9/1981 | Jones |
| 4,413,779 A | 11/1983 | Santini |
| 4,454,987 A | 6/1984 | Mitchell |
| 4,549,250 A | 10/1985 | Spector |
| 4,837,421 A | 6/1989 | Luthy |
| 4,849,606 A | 7/1989 | Martens et al. |
| 4,913,350 A | 4/1990 | Purzycki |
| 4,968,487 A | 11/1990 | Yamamoto et al. |
| 5,000,383 A | 3/1991 | van der Heijden |
| 5,038,394 A | 8/1991 | Hasegawa et al. |
| 5,290,546 A | 3/1994 | Hasegawa et al. |
| 5,364,027 A | 11/1994 | Kuhn |
| 5,556,192 A | 9/1996 | Wang |
| 5,937,140 A | 8/1999 | Leonard et al. |
| 6,478,440 B1 | 11/2002 | Jaworski et al. |
| 6,514,467 B1 * | 2/2003 | Bulsink et al. ............. 422/122 |
| 6,537,061 B1 * | 3/2003 | Gomez et al. .............. 431/268 |
| 6,580,875 B2 * | 6/2003 | Rymer ........................ 392/395 |

FOREIGN PATENT DOCUMENTS

WO    WO 0230220 A1    4/2002

* cited by examiner

*Primary Examiner*—Thomas Denion
*Assistant Examiner*—Jaime Corrigan

(57) ABSTRACT

A device that can be used for dispersing or dispensing a liquid is provided that comprises a container, a nozzle device, a secondary wick, and a control device in which the container comprises, an open end and a liquid; the nozzle comprises a primary wick, a first end being in fluid communication with the liquid, and a second end extending through the open end of the container and having an opening; the aperture has extended therethrough the primary wick; the secondary wick extends into proximity with the primary wick; and the secondary wick is securely connected to a control device, which controls the distance between the primary wick and the secondary wick.

18 Claims, 3 Drawing Sheets

LIQUID DISPERSION DEVICE

FIELD OF INVENTION

The present invention relates to a device comprising two or more wicks for dispersing a liquid for such purposes as, for example, dispensing fragrances and air fresheners, insecticides, air purifiers or disinfectants, aromatherapy, anticeptics, and other similar uses.

BACKGROUND OF INVENTION

The need for effective means of combating airborne odors in homes and public building by odor masking or destruction is well established as is the dispensing of insect control materials, aromatherapy, antiseptics and disinfectants. Various kinds of vapor-dispensing devices have been employed for these purposes. Common types of dispensing devices are aerosol containers which propel minute droplets of a liquid composition into the air, dish-like devices that support a gelatinous material which releases vapor upon drying, and wicking devices in which the liquid to be vaporized is transported through a wick and exposed to air. Air freshening devices in which there is a slow release of vapor into the air from a liquid are well known in the art. See, e.g., U.S. Pat. No. 1,994,932; U.S. Pat. No. 2,597,195; U.S. Pat. No. 2,802,695; U.S. Pat. No. 2,804,291; U.S. Pat. No. 2,942,090; U.S. Pat. No. 3,550,853; U.S. Pat. No. 3,780,260; U.S. Pat. No. 4,084,079; U.S. Pat. No. 4,286,754; U.S. Pat. No. 4,413,779; U.S. Pat. No. 4,454,987; U.S. Pat. No. 4,913,350; and U.S. Pat. No. 5,000,383. Also well known are wicking devices in which vaporization is enhanced by a heating source. See, e.g., U.S. Pat. No. 3,288,556; U.S. Pat. No. 3,431,393; U.S. Pat. No. 3,482,929; U.S. Pat. No. 3,633,881; U.S. Pat. No. 4,020,321; U.S. Pat. No. 4,968,487; U.S. Pat. No. 5,038,394; U.S. Pat. No. 5,290,546; U.S. Pat. No. 5,364,027; and U.S. Pat. No. 6,478,440. See also, U.S. Pat. No. 4,549,250; U.S. Pat. No. 4,837,421; U.S. Pat. No. 4,849,606; U.S. Pat. No. 5,556,192; U.S. Pat. No. 5,937,140; and WO02/30220.

However, current devices that rely on evaporation of the liquid from a wick have the disadvantages of depleting the liquid in a reservoir at an uneven rate and composition. See, e.g., U.S. Pat. No. 4,663,081. The cause for the change in the rate of evaporation is frequently the result of the evaporative surface of the wick becoming partially clogged during the evaporation process with less volatile resins. Compositional changes in the released vapor over time are also the result of uneven evaporation due to the more volatile components of the liquid mixture evaporating faster and thereby leaving a disproportionately different composition in the liquid from the original composition.

Therefore, it is highly desirable to derive a mass transfer device that disperses liquid into a vapor while substantially maintaining the liquid composition at the original composition over the useful life of the device, for example, 30 days. Further, it is desirable to have the ability to control the rate at which the liquid is dispersed and control it by electrical or mechanical means using timers, sensors, switches, or remote devices. It is especially desirable to be able to start and stop the dispersion of liquid to the vapor phase at will or even disperse different liquid solutions at different times. Further still, active ingredients in some instances need to be stable in solution and released only upon reaction with a second liquid or a catalytic surface.

SUMMARY OF THE INVENTION

Accordingly, the present invention provides a device for dispersing or dispensing a liquid that comprises a container, a nozzle device, a secondary wick, and a control device wherein the container comprises, an open end and a liquid;

the nozzle comprises a primary wick, a first end being in fluid communication with the liquid, and a second end extending through the open end of the container and having an opening; the aperture has extended therethrough the primary wick;

the secondary wick extends into proximity with the primary wick; and the secondary wick is securely connected to a control device, which controls the distance between the primary wick and the secondary wick.

DETAILED DESCRIPTION OF THE INVENTION

Figure 1:
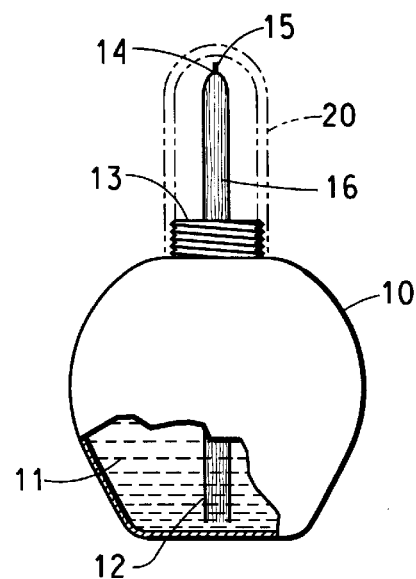
FIG. 1 is a partial cut-away view of container.

A preferred container or reservoir 10 is illustrated in FIG. 1. Container 10 can be any conventional vessel, bottle, or similar device and can be sealed with a closure or cap 20. Container 10 can contain a liquid or fluid 11 to be dispensed or dispersed. A preferred container is a rounded bottle having a nozzle device 12. Nozzle 12 can be any shape or form and is preferably a substantially tubular form. One end of nozzle 12 is in fluid communication with fluid 11. The other end 14 preferably extends upwardly through container opening 13. End 14 has an aperture or opening of about 0.01, to about 5 mm in diameter, preferably about 0.1 mm to about 5 mm, and more preferably <1.5 mm. The portion of nozzle device 12 extended outside opening 13 can be any length so long as it can reasonably disperse liquid 11 through nozzle 12 such as, for example, about 1 to about 50 mm. The nozzle device can be made from any material such as, for example, a polymer or plastic such as polypropylene, polyethylene, polybutylene, polyethylene terephthalate, nylon, or a metal or glass. Preferably, it is made of the same material that makes up container 10 such as, for example, plastics. The nozzle is about 2 mm to about 15 mm, preferably about 5 mm to about 10 mm, in diameter. Inside the nozzle, it comprises a wick (reference numeral 16), frequently referred to as primary wick herein, that can be made of any material that wicks such as, for example, cotton, polypropylene fibers, glass fiber, or any other material commonly used for wicking purposes or combinations of two or more thereof. Primary wick 16 is preferably outwardly and upwardly extending through the aperture of end 14 to about 0.01 to about 5 mm, more preferably less than 1 mm, atop of end 14 and is referred to as tip 15 in FIG. 1. Opening 13 is preferably externally threaded or has a press-fit connection for easy connection to cap 20. If opening 13 is externally threaded, cap 20 has an internally threaded connection at container opening 13. Though end 14 can be any shape, it is preferred end 14 be conical such as, for example, a sharp conical shape.

Container 10 can be combined with a secondary wick or wicking device 31 for dispensing liquid 11. Secondary wick 31 can have a surface area exposed to air or vapor that is at least twice, preferably five times, more preferably at least 15 times, and most preferably greater than 25 times larger than the exposed surface of the primary wick. Each of the primary and secondary wicks may be a sheet of wicking composition in a planar form, in an inverted or upright basket form, in cylinder form, in a spherical form, in a cone form, a bowel form, or any other forms depending on the need and one's preference. It can also be in the form of cotton balls or glass wool like materials or can be of a sponge like composition. Wicks 16 and 31, especially secondary wick 31, optionally can be coated thereon with a reactive or catalytic surface for the purpose of enhancing chemical reactions that release active components. Secondary wick 31 may also comprise or be impregnated thereon or therewith a material that can react instantly with liquid 11 thereby producing a second product to provide, for example, air deodorizing. The primary wick and secondary wick may be made of the same or different wicking materials. Examples include glass fibers; glass wool; natural polymers such as cellulose such as paper and cotton; synthetic polymers such as polyethylene, polypropylene, polybutylene, polyethylene terephthalate, various rubbers, elastomers, and nylon; or combinations of two or more thereof. The material can be in the form of paper, cloth, fibers, porous sponge, wick-based writing pens, or combinations of two or more thereof.

Figure 2A:
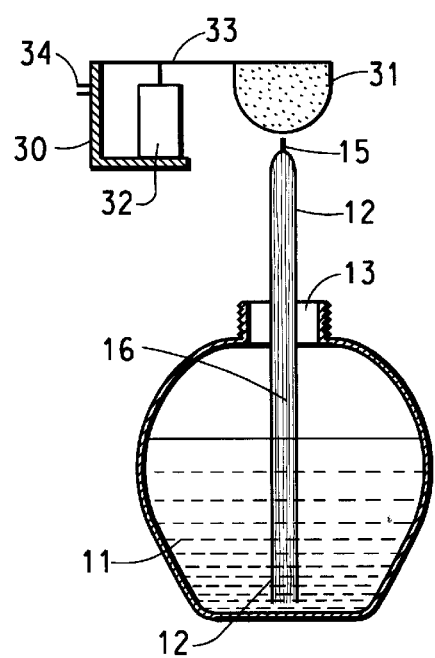
FIG. 2A shows the container with a secondary wick controlled by a solenoid showing the atmosphere exposed tip of the primary wick, such that the primary wick protrudes through the aperture of the nozzle.
Figure 2B:
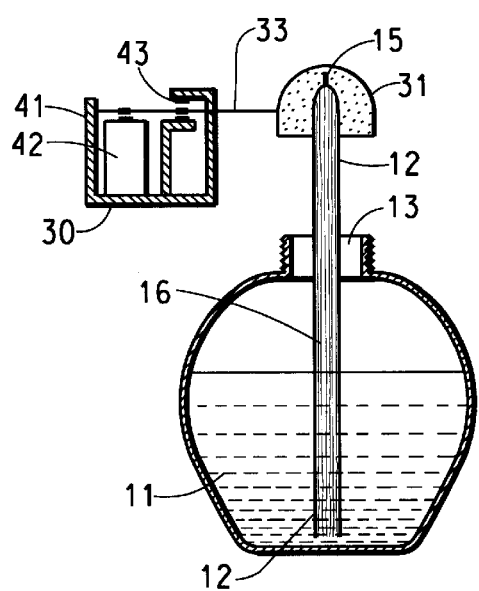
FIG. 2B illustrates the container with a secondary wick powered by a relay having a coil and contacts.
Figure 2C:
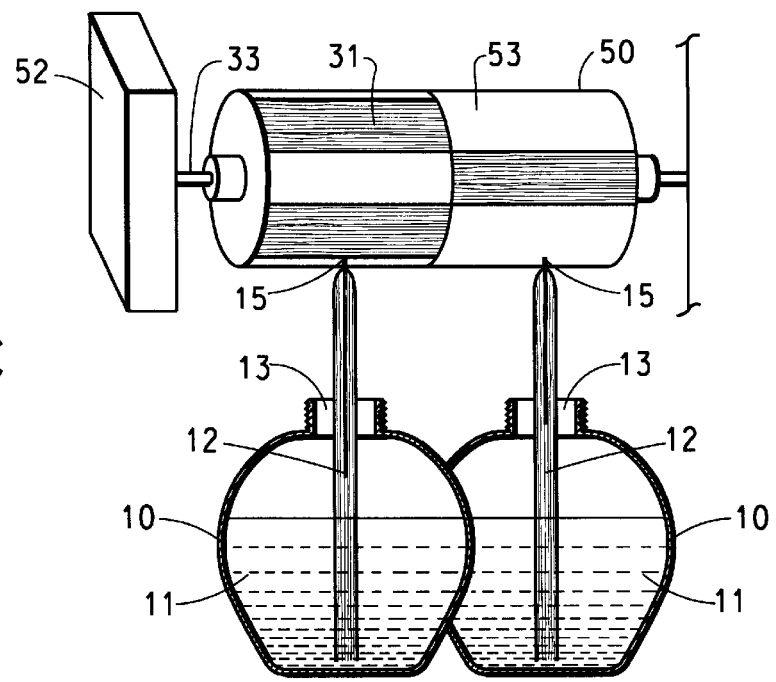
FIG. 2C shows two containers in contact with a drum having a secondary wicking and non-wicking surfaces powered by a motor.
Figure 2D:
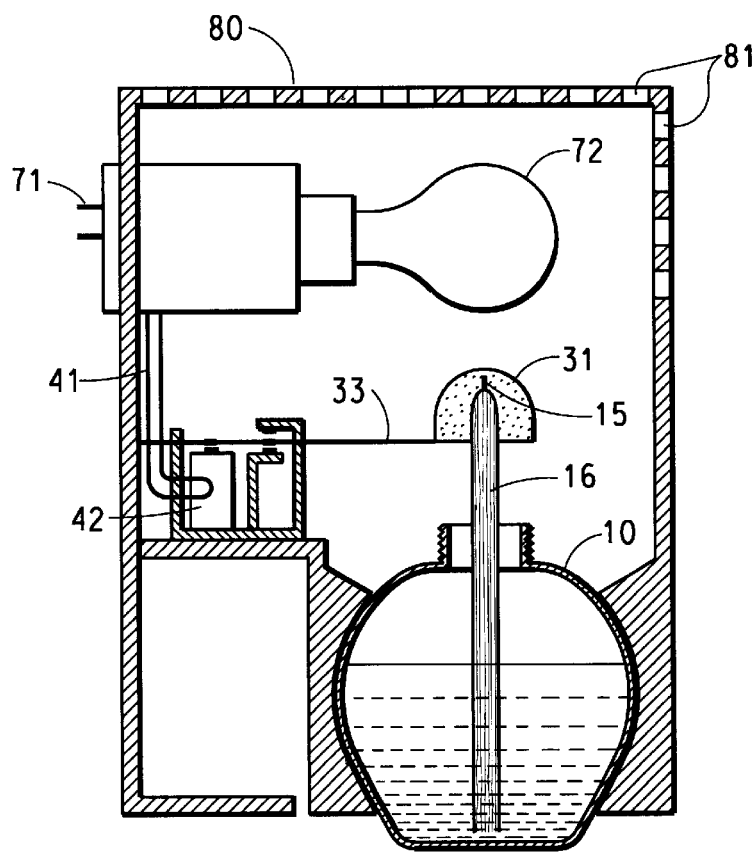
FIG. 2D shows one embodiment of the device which incorporates primary wick, secondary wick, a relay, power input, a heater which may also be a nightlight, and housing having perforated ventilation.
Figure 2E:
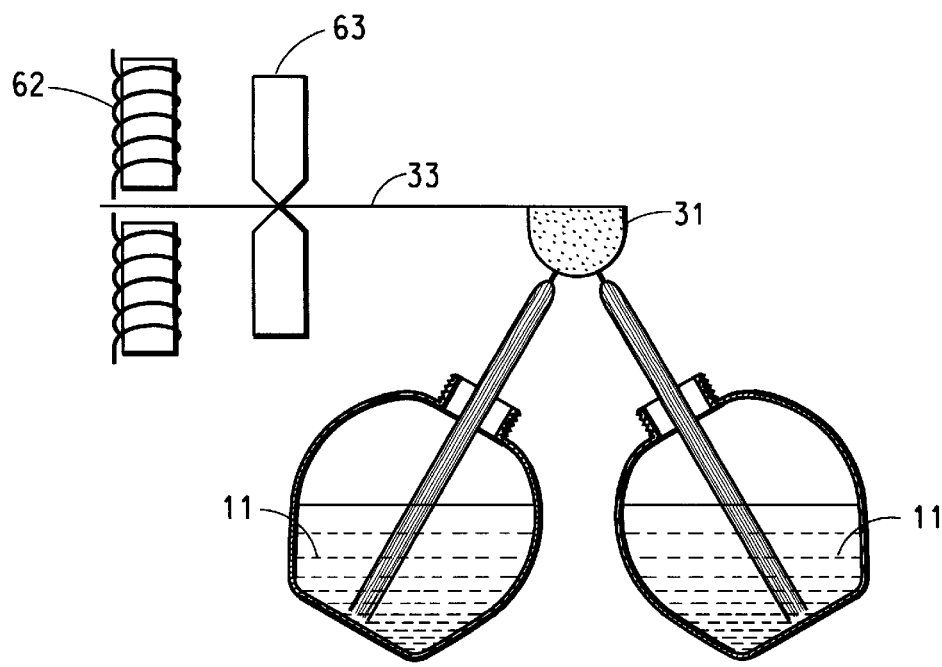
FIG. 2E shows two containers which may contain different liquids wicking onto a single secondary wick.

FIGS. 2A, 2B, 2C, 2D, and 2E illustrate some preferred embodiments of the invention. In FIG. 2A, a wicking device 30 comprises secondary wick 31, which is in closed proximity with tip 15 of container 10, and a control device 32, which controls the distance between wick 31 and tip 15. Wick 31 can be any form or shape disclosed above. Shown in FIGS. 2A and 2E is a bowel or basket shape. Shown in FIGS. 2B and 2D is a reversed bowel or basket shape. FIG. 2C shows a drum shape. The term "proximity" refers to a close distance between two subjects. The distance herein refers to that between the outer layer of wick 31 and tip 15 of primary wick 16 and can be in the range of from intimate contact to about 15 mm. The secondary wick can be of any length, size or thickness such as, using the basket shape shown in FIGS. 2A and 2E (as example, 0.5–5 cm circumference; 0.01–5 cm depth, and 0.01–50 mm thickness).

The primary and secondary wicks are preferably capable of moving with respect to one another in order to make or break contact between these two wicks. As such, when the primary and secondary wicks are in contact, liquid 11 can flow from the primary wick to the secondary wick until the secondary wick becomes saturated with liquid 11 being wicked from container 10. A means may be provided to move the primary and secondary wicks with respect to one another in order to provide contact of the wicks such that liquid can flow from the primary wick to the secondary wick or move apart to stop such flow. Examples of suitable means can be manual or by an electrically-driven means that can be controlled with a switching device, a timing device, a sensor, remotely, or by other means. Also, examples of suitable means includes the use of a heating device near the secondary wick to aid evaporation such as, for example, a resistive heater or a nightlight.

In addition to wick 31, wicking device 30 can comprise a control device 32 (FIG. 2A), 42 (FIGS. 2B and 2D), 52 (FIG. 2C), or 62 (FIG. 2E), which can be linked to wick 31 by a connecting means 33 such as, for example, metal or plastics. A control device is used to adjust the proximity between the primary wick and secondary wick. Any device that can automatically or manually control the movement can be used. Because such a control device is well known to one skilled in the art, detailed description of the device is omitted herein for the interest of brevity. A few examples are shown in these figures. For example, the control device shown in FIG. 2A is a solenoid that acts like a magnet when a current passes through it thereby controlling the movement of secondary wick 31. The control device shown in FIG. 2B and 2D is powered by a relay 41 having a coil 42 and contacts 43. The control device shown in FIG. 2C is powered by motor 52 which, for example, may be a clock motor for the purpose of alternatively dispersing two different liquids. In FIG. 2C, two containers 10 are each in contact with a drum 50 having wick 31 and a non-wicking material 53.

FIG. 2D shows an embodiment of the device which contains container 10 incorporating primary wick 16 and secondary wick 31, relay 41, power input 71, a heater 72 which may also serve as a nightlight, and housing 80 which can be made from, for example, a polymeric material and shows perforated ventilation 81 for vapor escape to atmosphere.

FIG. 2E shows another embodiment of the invention device comprising two containers in which each container 10 can comprise different liquids 11, each being stable under ambient conditions, wicking onto a single secondary wick 31 that may have contained thereon a catalyst. The liquids may, upon being wicked to the secondary wick, react to produce a desired product such as, for example, an odor eliminator. The secondary wick can be moved by the action of an electromagnet 62 coupling with fulcrum 63, as shown in FIG. 2E or by any means known to one skilled in the art. The wick is shown to be moved by the action of an electromagnet but may be moved by any means including a motor which may be a timing device. One of the liquids may be a solution of comprising active ingredient(s) in a stable form and the other a solution that can react with the stable form upon contact at secondary wick 31. Alternatively, wick 31 can be catalytically active or comprise a catalyst to catalyze the reaction between these liquids producing another fluid, preferably in vapor or gas form, such as, for example, a disinfectant or odor eliminator such as, for example, chlorine dioxide.

Figure 3:
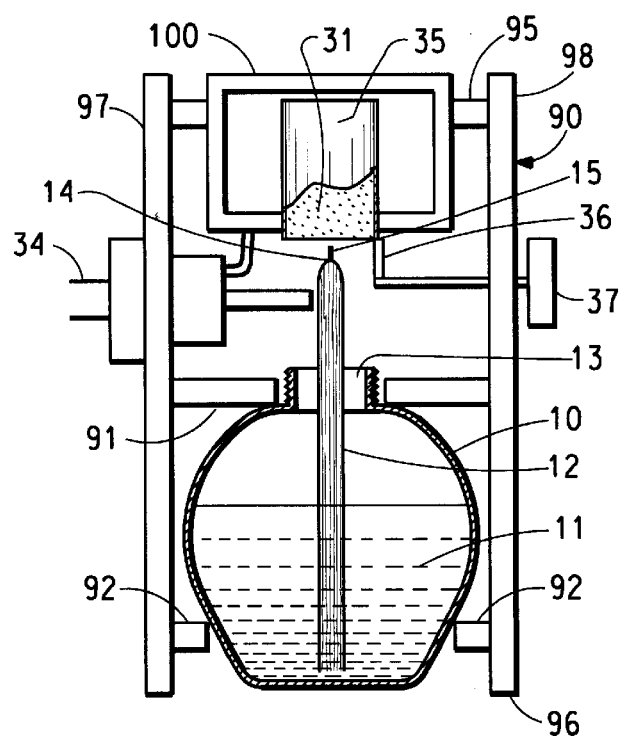
FIG. 3 is a view of a preferred embodiment of the device.

Shown in FIG. 3 is a preferred device that comprises housing 90 and container 10. Container 10 holds liquid 11 that can be dispersed as vapor. Upwardly secured within container 10 is nozzle 12 that extends through opening end 13 of container 10. One end of nozzle 12 is in fluid communication with liquid 11. The nozzle can comprise primary wick 16 that protrudes through nozzle end 14 as tip 15. The portion of the primary wick that is outside tip 14 is within about 0.01 to about 5 mm. The shorter the tip atop end 14, the slower rate of evaporation of liquid 11.

Container 10 can be secured in housing 90 which has an upper end 95, a lower end 96, each end having an opening, first wall 97, and second wall 98. For example, container 10 can fit snuggly into the housing and snaps into place by deformations 91 and/or 92 of walls 97 and 98 of housing 90. Housing 90 optionally can contain heating element 100 (with electrical input 34), which is preferably located at the opposite end container 10 and a removable second housing 35, preferably in cylindrical shape, which can be made of a material such as ceramic, metal, glass, polymer, plastic, or the like, or combinations of these, and comprises secondary wick 31. A cylinder is used herein to illustrate second housing 35, though other shapes can be readily used. Cylinder 35 can be secured within housing 90 at the opening of the heating element so that it readily moves within the opening in the preferred embodiment in a vertical motion. For example, cylinder 35 rests on a stop 36, which can move the cylinder so that the secondary wick is either in contact with primary wick tip 15 or not in contact with the primary wick. This stop device can be, for example, an on/off switch 37 and may be operated manually or by electrical means. The preferred position of the secondary wick with respect to the cylinder is on the lower opening of the cylinder (the opening nearest to the primary wick). This cylinder can be heated by heating element 100 which transfers the heat to the outer rim of the secondary wick to enhance evaporation of wicked liquid. The primary wick is located so that heat transfer from the heater to the primary wick is inefficient. Heating may be useful for compositions that contain low volatility liquids. Alternative heat source can by resistive heating, by using a nightlight, or by other means. Also included is a container that holds the liquid to be dispersed that is separate from the housing device in which the electronics and the secondary wick or wicks are housed. The separate container allows refills to be inserted into the housing.

In summary, FIG. 2A is an embodiment showing primary and secondary wicks, and a solenoid to move the secondary wick in and out of contact with the primary wick. FIG. 2B shows a similar embodiment but with the secondary wicking device moved into and out of contact with the atmosphere exposed primary wicking surface by a relay device. The control in FIG. 2A or 2B causing the secondary wick to move could be replaced by a simple lever to manually move the secondary wick or by other electronic devices including motors. FIG. 2C shows that more than one container can be used to disperse two liquids via secondary wicks on a drum device. While the primary wick from one container device contacts the secondary wick on a drum surface, the primary wick of the second container is either not making contact with a surface or is contacting a non-wicking surface. The drum in this case turns so that each primary wick alternatively contacts wicking and non-wicking surfaces. The drum can be turned by a clock motor to make it a time release device. FIG. 2D shows a container within a housing that also holds a device for moving the secondary wick in and out of contact with the primary wick's atmosphere exposed surface. A heating device may be incorporated to aid evaporation of liquid from the secondary wick surface. A means of supplying current is provided which may be 110 or 220 V AC or by battery. The device for moving the secondary wick with respect to the primary wick can be activated by manual control, a switch, a timing device, a sensor, by a remote signal, and the like. FIG. 2E demonstrates a means of using this invention to release active ingredients that are in a stable form by reaction at the secondary wick surface with a second liquid containing a reactive element. FIG. 2E also shows two primary wicks from separate reservoirs of liquid contacting the same secondary wick to cause a chemical reaction to release the desired active ingredients of components.

The liquid to be dispersed by the device described here may be selected from a large variety of materials suitable for vaporization into the atmosphere, such as the active ingredients selected from such groups as air fresheners, fragrances, aroma therapy, odor counteractants and eliminators, deodorizers, antiseptics, disinfectants, sanitizers, insecticides, insect repellants, medicinal compounds, and mixtures thereof. Fragrances and air fresheners are the most commonly employed among these and comprise one or more organic compounds that are available from perfumery suppliers such as Quest and International Flavors & Fragrances in the US as well as other vendors or manufacturers such as Givaudan-Roure, Firmenich, Noville, and Takasago. These materials may be synthetically or naturally derived and may contain such compounds as ketones, aldehydes, esters, alcohols, terpenes, acetates, oils, solvents, and the like. Fragrances can be simple in composition or a complex mixture of natural and synthetic compounds.

It is desired that the composition of the liquid in container 10 does not change appreciably even after continuous use for as much as 10 days, preferably 20 days, and more preferably 30 days. Unlike evaporative devices in which the most volatile components are dispersed at a faster rate than less volatile components from the primary wick, in this device, the primary wick acts to transfer liquid to the second wick. Only a small area of the primary wick is exposed to air from which evaporation can occur, but when in contact with the secondary wick, liquid flows from the primary wick to the secondary wick, assuming the secondary wick is not saturated with liquid. This flow of liquid propelled by the surface tension of the liquid and herein referred to as wicking, causes any residue on the primary wick to be dissolved and transferred to the secondary wick. This mechanism minimizes compositional changes in the liquid in the reservoir and in the primary wicking material. Residue buildup can occur on the secondary wicking material, but because the liquid flow in the secondary wick is away from the point of contact of the two wicks, the residue builds up at the outermost areas of liquid wicking and thus contributes minimally to clogging of the secondary wick. The evaporative surface of the secondary wick is preferably at least 5 times and preferably greater than 25 times that of the primary wick. Large surface area secondary wicks further reduce problems associated with clogging. Also, wicks that rotate on a drum surface, as shown in FIG. 2D, exposing fresh surface by the act of movement relative to the primary wick are also less prone to clogging.

Compositional changes caused by less volatile components building up at the evaporative surface of wicks result in a slow change in the liquid released. In addition, prolonged release of the same liquid results in olfactory fatigue. In the device disclosed herein, these deficiencies can be reduced by operating the device in a mode that turns off liquid flow between the wicks for substantial periods of time; for example, overnight. Once contact between the two wicks is broken, liquid flow from the primary to the secondary wick ceases. Evaporation from the primary wick surface is minimal because of the low surface area exposed to air. Liquid evaporating from the secondary wick is not replaced and the wick begins to dry, resulting is a decrease in vapors emanating from the secondary wick. Low volatility components remaining on the wick release at a slower rate than the more volatile components and without liquid transfer between wicks eventually falls below the threshold of olfactory detection. This process can be made faster by application of heat to the secondary wick. Continued evaporation below the detection threshold cleans the wicking surface for the next contact period. During the time the wicks are not in contact, liquid is dispensed from the container at a very low rate by evaporation from the small surface area of the primary wick that is exposed to atmosphere. The slow rate of liquid dispersion in the "off" position vs. the "on" position preserves liquid and extends the useful life of the device. If desired, a second and different liquid could be dispersed during the time the first liquid is in the off or no contact mode.

The invention device provides a control mechanism for the rate of evaporation by either the amount of surface area of the secondary wick exposed to atmosphere or by the time the two wicks contact one another. Wishing not to be bound by theory, the shorter the contact time the less liquid can be available for dispersion by evaporation from the secondary wick. Likewise, secondary wicks having low surface area when saturated with liquid can disperse less vapor than a larger surface area wick that likewise is saturated. Once either wick is saturated, liquid flow can equal the rate of evaporation. The rate of evaporation from the larger surface area wick is, in theory, higher; the amount of liquid dispersed is also higher. Thus, the rate of liquid dispersion can be controlled manually by either causing the wicks to be in contact with one another or be separated, or by selecting among wicks of different sizes. Likewise, electronic control of the liquid to vapor dispersion rate can be by similar mechanisms. Electronic control can be through switches, sensors, timers, remote devices, and the like.

What is claimed is:

1. A device comprising a container, a nozzle, a secondary wick, and a control device wherein said container comprises an open end and a liquid;

said nozzle comprises a primary wick, a first end being fixedly secured within said container and being in fluid communication with said liquid, and a second end extending through said open end and having an aperture; said aperture has extended therethrough said primary wick;

said secondary wick extends into proximity with said primary wick; and aid secondary wick is securely connected to a control device, which controls the distance between said primary wick and said secondary wick.

2. A device according to claim 1 wherein said aperture is between 0.01 and 5 mm in diameter.

3. A device according to claim 1 wherein said aperture is <1.5 mm in diameter.

4. A device according to claim 1 wherein the surface area of said secondary wick is at least 5 times the surface area of said primary wick and the surface area refers to area exposed to atmosphere.

5. A device according to claim 4 wherein the surface area of said secondary wick is at least 25 times the surface area of said primary wick.

6. A device according to claim 5 wherein said aperture is <1.5 mm in diameter.

7. A device according to claim 1 wherein said primary wick or secondary wick is made from papers, polymers, fibers, cotton, glass wool, sponge-like materials or combinations of two or more thereof.

8. A device according to claim 7 wherein said aperture is <1.5 mm in diameter.

9. A device according to claim 8 wherein said liquid is one or more air fresheners, fragrances, aroma therapy, odor counteractants and eliminators, deodorizers, anticeptics, disinfectants, sanitizers, insecticides, insect repellants, medicinal compounds, or combinations of two or more thereof.

10. A device according to claim 9 wherein said secondary wick comprises a catalyst.

11. A device according to claim 9 wherein said control device is solenoid, relay, motor, or electromagnet device.

12. A device according to claim 1 wherein said secondary wick comprises a catalyst.

13. A device according to claim 1 further comprising a housing wherein said housing has first wall, second wall, and said container and a second housing secured therewithin; and said second housing comprises said secondary wick.

14. A device according to claim 13 wherein said aperture is between 0.01 and 5 mm in diameter.

15. A device according to claim 14 wherein the surface area of said secondary wick is at least 25 times the surface area of said primary wick.

16. A device according to claim 15 wherein said primary wick or secondary wick is made from filter papers, polymers, fibers, cotton, glass wool, sponge-like materials or combinations of two or more thereof.

17. A device according to claim 13 wherein said primary wick or secondary wick is made from filter papers, polymers, fibers, cotton, glass wool, sponge-like materials or combinations of two or more thereof.

18. A device according to claim 16 wherein said secondary wick comprises a catalyst.

* * * * *